United States Patent
Hollis

(10) Patent No.: US 9,770,571 B2
(45) Date of Patent: *Sep. 26, 2017

(54) VENT VALVE ASSEMBLY

(71) Applicant: ResMed Limited, Bella Vista, New South Wales (AU)

(72) Inventor: Shane Douglas Hollis, Auckland (NZ)

(73) Assignee: ResMed Limited, Bella Vista (AU)

( * ) Notice: Subject to any disclaimer, the term of this patent is extended or adjusted under 35 U.S.C. 154(b) by 276 days.

This patent is subject to a terminal disclaimer.

(21) Appl. No.: 14/632,230

(22) Filed: Feb. 26, 2015

(65) Prior Publication Data

US 2015/0190606 A1    Jul. 9, 2015

Related U.S. Application Data

(60) Continuation of application No. 11/404,870, filed on Apr. 17, 2006, now Pat. No. 8,997,739, which is a (Continued)

(30) Foreign Application Priority Data

Oct. 16, 1996    (AU) ..................................... PO3017

(51) Int. Cl.
    *A61M 16/20* (2006.01)
    *A61M 16/06* (2006.01)
    *A62B 9/02* (2006.01)

(52) U.S. Cl.
    CPC .......... *A61M 16/201* (2014.02); *A61M 16/06* (2013.01); *A61M 16/208* (2013.01);
    (Continued)

(58) Field of Classification Search
    CPC .. A61M 16/06; A61M 16/201; A61M 16/208; A61M 16/209; A61M 2205/42;
    (Continued)

(56) References Cited

U.S. PATENT DOCUMENTS

| 1,926,027 A | 9/1933 | Biggs |
| 2,123,353 A | 7/1938 | Catt |
(Continued)

FOREIGN PATENT DOCUMENTS

| AU | A-62221/90 | 3/1991 |
| AU | 91/77110 B | 11/1991 |
(Continued)

OTHER PUBLICATIONS

Parent; U.S. Appl. No. 11/404,870, filed Apr. 17, 2006, Hollis.
(Continued)

*Primary Examiner* — Kari Rodriquez
*Assistant Examiner* — Raymond E Harris
(74) *Attorney, Agent, or Firm* — Nixon & Vanderhye P.C.

(57) ABSTRACT

A vent valve apparatus (10) for use with a system for supplying breathable gas pressurised above atmospheric pressure to a human or animal. The apparatus (10) includes a gas washout vent (15), a vent valve (18) adapted to progressively restrict the flow area of the washout vent (15), and a pressure sensitive vent valve control means (20,22, 23). The control means is adapted to progressively cause the vent valve (18) to restrict the flow area of the gas washout vent (15) in response to increases in the pressure of the gas supply, thereby substantially regulating the volumetric flow of gas and/or $CO_2$ gas through the washout vent (15) over a range of gas supply pressures.

16 Claims, 3 Drawing Sheets

Related U.S. Application Data continuation of application No. 11/094,174, filed on Mar. 31, 2005, now Pat. No. 7,059,325, which is a continuation of application No. 10/365,397, filed on Feb. 13, 2003, now Pat. No. 6,889,692, which is a division of application No. 09/361,495, filed on Jul. 26, 1999, now Pat. No. 6,557,555, which is a continuation of application No. 08/951,357, filed on Oct. 16, 1997, now Pat. No. 6,006,748.

(52) U.S. Cl.
CPC ... *A61M 16/209* (2014.02); *A61M 2205/3331* (2013.01); *A61M 2205/42* (2013.01); *A61M 2250/00* (2013.01); *A62B 9/02* (2013.01); *Y10S 137/908* (2013.01); *Y10T 137/2617* (2015.04); *Y10T 137/7781* (2015.04); *Y10T 137/7786* (2015.04)

(58) Field of Classification Search
CPC ....... A61M 2205/3331; A61M 2250/00; Y10T 137/908; Y10T 137/2617; Y10T 137/7781; Y10T 137/7786; A62B 9/02
See application file for complete search history.

(56) References Cited

U.S. PATENT DOCUMENTS

| | | |
|---|---|---|
| 2,248,477 A | 7/1941 | Lombard |
| 2,254,854 A | 9/1941 | O'Connell |
| 2,317,608 A | 4/1943 | Heidbrink |
| 2,371,965 A | 3/1945 | Lehmberg |
| 2,438,058 A | 3/1948 | Kincheloe |
| 2,519,349 A | 8/1950 | Burns et al. |
| 2,774,346 A * | 12/1956 | Halliburton ............ A61M 16/00 128/200.21 |
| 2,931,356 A | 4/1960 | Schwarz |
| D188,084 S | 5/1960 | Garelick |
| 2,939,458 A | 6/1960 | Lundquist |
| 3,013,556 A | 12/1961 | Galleher |
| 3,189,027 A | 6/1965 | Bartlett |
| 3,238,943 A | 3/1966 | Holley |
| 3,315,674 A | 4/1967 | Bloom et al. |
| 3,330,273 A | 7/1967 | Bennett |
| 3,362,420 A | 1/1968 | Blackburn et al. |
| 3,363,833 A | 1/1968 | Laerdal |
| 3,556,122 A | 1/1971 | Laerdal |
| 3,580,051 A | 5/1971 | Blevins |
| 3,643,686 A | 2/1972 | Koegel |
| 3,700,000 A | 10/1972 | Hesse et al. |
| 3,783,893 A | 1/1974 | Davison |
| 3,796,216 A | 3/1974 | Schwarz |
| D231,803 S | 6/1974 | Huddy |
| 3,903,875 A | 9/1975 | Hughes |
| 3,932,054 A | 1/1976 | McKelvey |
| 3,985,467 A | 10/1976 | Lefferson |
| 3,992,598 A | 11/1976 | Welsh et al. |
| 4,077,404 A | 3/1978 | Elam |
| D250,131 S | 10/1978 | Lewis et al. |
| 4,167,185 A | 9/1979 | Lewis |
| 4,226,234 A | 10/1980 | Gunderson |
| 4,230,147 A | 10/1980 | Booth et al. |
| 4,245,632 A | 1/1981 | Houston |
| 4,249,527 A | 2/1981 | Ko et al. |
| 4,301,833 A | 11/1981 | Donald |
| D262,322 S | 12/1981 | Mizerak |
| 4,304,229 A | 12/1981 | Curtin |
| 4,306,585 A | 12/1981 | Manos |
| 4,316,458 A | 2/1982 | Hammerton-Fraser |
| 4,328,797 A | 5/1982 | Rollins, III et al. |
| 4,345,593 A | 8/1982 | Sullivan |
| 4,347,205 A | 8/1982 | Stewart |
| 4,354,488 A | 10/1982 | Bartos |
| 4,378,011 A | 3/1983 | Warncke et al. |
| 4,383,550 A | 5/1983 | Sotokazu |
| 4,387,722 A | 6/1983 | Kearns |
| 4,402,316 A | 9/1983 | Gadberry |
| 4,412,537 A | 11/1983 | Tiger |
| 4,436,090 A | 3/1984 | Darling |
| 4,440,163 A | 4/1984 | Spergel |
| 4,448,058 A | 5/1984 | Jaffe et al. |
| 4,467,799 A | 8/1984 | Steinberg |
| 4,522,639 A | 6/1985 | Ansite et al. |
| 4,530,334 A | 7/1985 | Pagdin |
| 4,608,976 A | 9/1986 | Suchy |
| 4,616,647 A | 10/1986 | McCreadie |
| 4,622,964 A | 11/1986 | Flynn |
| 4,655,213 A | 4/1987 | Rapoport et al. |
| 4,665,570 A | 5/1987 | Davis |
| 4,671,271 A | 6/1987 | Bishop et al. |
| 4,677,977 A | 7/1987 | Wilcox |
| 4,686,974 A | 8/1987 | Sato et al. |
| D293,613 S | 1/1988 | Wingler |
| 4,770,169 A | 9/1988 | Schmoegner et al. |
| 4,774,941 A | 10/1988 | Cook |
| 4,782,832 A | 11/1988 | Trimble et al. |
| 4,791,956 A | 12/1988 | Kominami et al. |
| 4,795,314 A | 1/1989 | Prybella et al. |
| 4,809,692 A | 3/1989 | Nowacki et al. |
| 4,821,713 A | 4/1989 | Bauman |
| 4,827,922 A | 5/1989 | Champain et al. |
| 4,838,258 A | 6/1989 | Dryden et al. |
| 4,841,953 A | 6/1989 | Dodrill |
| 4,848,334 A | 7/1989 | Bellm |
| 4,848,366 A | 7/1989 | Aita et al. |
| 4,870,963 A | 10/1989 | Carter |
| 4,898,167 A | 2/1990 | Pierce et al. |
| 4,907,584 A | 3/1990 | McGinnis |
| 4,910,806 A | 3/1990 | Baker et al. |
| 4,913,401 A | 4/1990 | Handke |
| 4,919,128 A | 4/1990 | Kopala et al. |
| 4,938,212 A | 7/1990 | Snook et al. |
| 4,944,310 A | 7/1990 | Sullivan |
| D310,431 S | 9/1990 | Bellm |
| 4,957,107 A | 9/1990 | Sipin |
| 4,971,051 A | 11/1990 | Toffolon |
| 4,989,599 A | 2/1991 | Carter |
| 5,005,568 A | 4/1991 | Loescher et al. |
| 5,005,571 A | 4/1991 | Dietz |
| 5,009,635 A | 4/1991 | Scarberry |
| 5,024,219 A | 6/1991 | Dietz |
| 5,038,776 A | 8/1991 | Harrison et al. |
| 5,042,473 A | 8/1991 | Lewis |
| 5,042,478 A | 8/1991 | Kopala et al. |
| 5,046,200 A | 9/1991 | Feder |
| 5,065,756 A | 11/1991 | Rapoport |
| 5,069,205 A | 12/1991 | Urso |
| 5,105,354 A | 4/1992 | Nishimura |
| 5,109,840 A | 5/1992 | Daleiden |
| 5,117,819 A | 6/1992 | Servidio et al. |
| 5,121,745 A | 6/1992 | Israel |
| 5,133,347 A | 7/1992 | Huennebeck |
| 5,134,995 A | 8/1992 | Gruenke et al. |
| 5,140,982 A | 8/1992 | Bauman |
| 5,148,802 A * | 9/1992 | Sanders ................ A61M 16/00 128/204.18 |
| 5,161,525 A | 11/1992 | Kimm et al. |
| 5,174,332 A | 12/1992 | Yokoyama et al. |
| 5,183,983 A | 2/1993 | Knop |
| D334,633 S | 4/1993 | Rudolph |
| 5,199,424 A | 4/1993 | Sullivan et al. |
| 5,203,343 A | 4/1993 | Axe et al. |
| 5,231,979 A | 8/1993 | Rose et al. |
| 5,239,995 A | 8/1993 | Estes et al. |
| 5,243,971 A | 9/1993 | Sullivan et al. |
| 5,245,995 A | 9/1993 | Sullivan et al. |
| 5,259,373 A | 11/1993 | Gruenke et al. |
| 5,265,595 A | 11/1993 | Rudolph |
| 5,271,391 A | 12/1993 | Graves |
| 5,279,289 A | 1/1994 | Kirk |
| 5,305,787 A | 4/1994 | Thygesen |
| 5,313,937 A | 5/1994 | Zdrojkowski |
| 5,335,654 A | 8/1994 | Rapoport |

(56) References Cited

U.S. PATENT DOCUMENTS

| | | |
|---|---|---|
| 5,343,878 A | 9/1994 | Scarberry et al. |
| 5,353,788 A | 10/1994 | Miles |
| 5,357,951 A | 10/1994 | Ratner |
| 5,419,318 A | 5/1995 | Tayebi |
| 5,429,126 A | 7/1995 | Bracken |
| 5,429,683 A | 7/1995 | Le Mitouard |
| 5,431,158 A | 7/1995 | Tirotta |
| 5,433,193 A | 7/1995 | Sanders et al. |
| 5,438,981 A | 8/1995 | Starr et al. |
| 5,441,046 A | 8/1995 | Starr et al. |
| 5,443,061 A | 8/1995 | Champain et al. |
| D362,061 S | 9/1995 | McGinnis et al. |
| 5,458,137 A | 10/1995 | Axe et al. |
| 5,477,852 A | 12/1995 | Landis et al. |
| 5,488,948 A | 2/1996 | Dubruille et al. |
| 5,490,502 A | 2/1996 | Rapoport et al. |
| 5,492,113 A | 2/1996 | Estes et al. |
| 5,492,116 A | 2/1996 | Scarberry et al. |
| 5,501,214 A | 3/1996 | Sabo |
| 5,503,146 A | 4/1996 | Froehlich et al. |
| 5,517,983 A | 5/1996 | Deighan et al. |
| 5,517,986 A | 5/1996 | Starr et al. |
| 5,522,382 A | 6/1996 | Sullivan et al. |
| RE35,295 E | 7/1996 | Estes et al. |
| 5,535,738 A | 7/1996 | Estes et al. |
| 5,535,739 A | 7/1996 | Rapoport et al. |
| 5,537,997 A | 7/1996 | Mechlenburg et al. |
| 5,540,219 A | 7/1996 | Mechlenburg et al. |
| 5,540,220 A | 7/1996 | Gropper |
| 5,540,223 A | 7/1996 | Starr et al. |
| 5,542,128 A | 8/1996 | Lomas |
| 5,542,416 A | 8/1996 | Chalvignac |
| 5,546,933 A | 8/1996 | Rapoport et al. |
| 5,551,418 A | 9/1996 | Estes et al. |
| 5,551,419 A | 9/1996 | Froehlich et al. |
| RE35,339 E | 10/1996 | Rapoport |
| 5,560,354 A | 10/1996 | Berthon-Jones et al. |
| 5,570,689 A | 11/1996 | Starr et al. |
| D377,089 S | 12/1996 | Starr et al. |
| 5,592,938 A | 1/1997 | Scarberry et al. |
| 5,598,838 A | 2/1997 | Servidio et al. |
| 5,617,846 A | 4/1997 | Graetz et al. |
| 5,632,269 A | 5/1997 | Zdrojkowski |
| 5,645,053 A | 7/1997 | Remmers et al. |
| 5,645,054 A | 7/1997 | Cotner et al. |
| 5,647,355 A | 7/1997 | Starr et al. |
| 5,647,357 A | 7/1997 | Barnett et al. |
| 5,655,522 A | 8/1997 | Mechlenburg et al. |
| 5,655,527 A | 8/1997 | Scarberry et al. |
| 5,657,752 A | 8/1997 | Landis et al. |
| 5,662,101 A | 9/1997 | Ogden et al. |
| 5,666,946 A | 9/1997 | Langenback |
| 5,682,878 A | 11/1997 | Ogden |
| 5,685,296 A | 11/1997 | Zdrojkowski |
| 5,687,715 A | 11/1997 | Landis et al. |
| 5,704,345 A | 1/1998 | Berthon-Jones |
| 5,715,812 A | 2/1998 | Deighan et al. |
| 5,715,814 A | 2/1998 | Ebers |
| 5,740,795 A | 4/1998 | Brydon |
| 5,746,201 A | 5/1998 | Kidd |
| 5,937,855 A | 8/1999 | Zdrojkowski et al. |
| 6,006,748 A | 12/1999 | Hollis |
| 6,557,555 B1 | 5/2003 | Hollis |
| 6,889,692 B2 | 5/2005 | Hollis |
| 7,059,325 B2 | 6/2006 | Hollis |
| 7,089,939 B2 | 8/2006 | Walker et al. |
| 7,174,893 B2 | 2/2007 | Walker et al. |
| 2005/0166923 A1 | 8/2005 | Hollis |

FOREIGN PATENT DOCUMENTS

| | | |
|---|---|---|
| AU | A-33877/93 | 4/1993 |
| AU | B-59270/90 | 5/1993 |
| AU | A-38508/93 | 7/1993 |
| AU | A-48748/93 | 9/1993 |
| AU | A-52628/93 | 7/1994 |
| AU | 94/64816 B | 12/1994 |
| AU | 95/16178 B | 7/1995 |
| AU | 9459430 | 2/1996 |
| AU | A 32914/95 | 2/1996 |
| AU | A-34471/95 | 2/1996 |
| AU | A-40711/95 | 4/1996 |
| AU | B 34354/95 | 5/1996 |
| AU | A 39130/95 | 6/1996 |
| AU | A 42027/97 | 2/1998 |
| AU | A 41018/97 | 4/1998 |
| DE | 459104 | 4/1928 |
| DE | 159396 | 6/1981 |
| DE | 3015279 A1 | 10/1981 |
| DE | 3345067 A1 | 6/1984 |
| DE | 3537507 A1 | 4/1987 |
| DE | 3539073 A1 | 5/1987 |
| DE | 4004157 C1 | 4/1991 |
| DE | 4343205 A1 | 6/1995 |
| DE | 4432219 C1 | 4/1996 |
| DE | 197 35 359 | 1/1998 |
| DE | 297 23 101 | 7/1998 |
| EP | 0 065 154 A1 | 10/1981 |
| EP | 0 066 451 A1 | 12/1982 |
| EP | 0 088 761 | 9/1983 |
| EP | 0 164 500 A2 | 3/1985 |
| EP | 0 171 321 A1 | 2/1986 |
| EP | 0 252 052 A1 | 1/1988 |
| EP | 0 264 772 A1 | 4/1988 |
| EP | 298 367 A2 | 1/1989 |
| EP | 0 386 605 A1 | 2/1990 |
| EP | 0 425 092 A1 | 5/1991 |
| EP | 0427474 A2 | 5/1991 |
| EP | 0 462 701 A1 | 12/1991 |
| EP | 481 459 A1 | 4/1992 |
| EP | 0549299 A2 | 6/1993 |
| EP | 0 602 424 | 11/1993 |
| EP | 606 687 A2 | 7/1994 |
| EP | 0 608 684 A1 | 8/1994 |
| EP | 0705615 A1 | 9/1994 |
| EP | 0 714 670 A2 | 12/1994 |
| EP | 0 656 216 A2 | 6/1995 |
| EP | 0 661 071 A1 | 7/1995 |
| EP | 0 697 225 | 7/1995 |
| EP | 178 925 A2 | 4/1996 |
| EP | 0 709 107 A1 | 5/1996 |
| EP | 0 747 078 A2 | 12/1996 |
| EP | 0 788 805 A2 | 8/1997 |
| EP | 0 821 978 | 2/1998 |
| FR | 2 574 657 A1 | 6/1986 |
| FR | 2 658 725 A1 | 8/1991 |
| FR | 2682042 A1 | 4/1993 |
| FR | 2 749 176 | 12/1997 |
| GB | 1432571 | 4/1976 |
| GB | 1 444 053 | 7/1976 |
| GB | 1 467 828 | 3/1977 |
| GB | 2 077 444 A | 12/1981 |
| GB | 2145335 A | 3/1985 |
| GB | 2 147 506 A | 5/1985 |
| GB | 2 164 569 A | 3/1986 |
| GB | 2 205 167 A | 11/1988 |
| GB | 2 254 700 A | 10/1992 |
| GB | 2 294 400 A | 5/1996 |
| JP | 54-104369 | 8/1979 |
| JP | 62-103297 | 4/1987 |
| JP | 63-275352 | 11/1988 |
| JP | 4-70516 A | 3/1992 |
| JP | 6-249742 A | 9/1994 |
| JP | 07280609 A | 10/1995 |
| JP | 8019610 A | 1/1996 |
| JP | 09/216240 A | 8/1997 |
| SE | 467041 B | 5/1992 |
| WO | WO 80/01044 | 5/1980 |
| WO | WO 82/03326 | 10/1982 |
| WO | WO 82/03548 | 10/1982 |
| WO | WO 86/05965 | 10/1986 |
| WO | WO 86/06969 | 12/1986 |
| WO | WO 88/10108 | 12/1988 |
| WO | WO 90/14121 | 11/1990 |

(56) References Cited

FOREIGN PATENT DOCUMENTS

| WO | WO 91/03277 | 3/1991 |
|---|---|---|
| WO | WO 92/11054 | 7/1992 |
| WO | WO 92/15353 | 9/1992 |
| WO | WO 92/20395 | 11/1992 |
| WO | WO 92/22244 | 12/1992 |
| WO | WO 93/01854 | 2/1993 |
| WO | WO 93/08867 | 5/1993 |
| WO | WO 93/09834 | 5/1993 |
| WO | WO 93/21982 | 11/1993 |
| WO | WO 93/24169 | 12/1993 |
| WO | WO 94/02190 | 2/1994 |
| WO | WO 94/16759 | 8/1994 |
| WO | WO 94/20051 | 9/1994 |
| WO | WO 94/23780 | 10/1994 |
| WO | WO 95/02428 | 1/1995 |
| WO | WO 95/32016 | 11/1995 |
| WO | WO 96/16688 | 6/1996 |
| WO | WO 96/17643 | 6/1996 |
| WO | WO 96/25983 | 8/1996 |
| WO | WO 96/39206 | 12/1996 |
| WO | WO 96/40337 | 12/1996 |
| WO | WO 97/02064 | 1/1997 |
| WO | WO 97/07847 | 3/1997 |
| WO | WO 97/10019 | 3/1997 |
| WO | WO 97/10868 | 3/1997 |
| WO | WO 97/15343 | 5/1997 |
| WO | WO 97/28838 | 8/1997 |
| WO | WO 97/41812 | 11/1997 |
| WO | WO 97/41911 | 11/1997 |
| WO | WO 98/04310 | 2/1998 |
| WO | WO 98/06449 | 2/1998 |
| WO | WO 98/11930 | 3/1998 |
| WO | WO 98/18514 | 5/1998 |
| WO | WO 98/24499 | 6/1998 |
| WO | WO 98/25662 | 6/1998 |
| WO | WO 98/26829 | 6/1998 |
| WO | WO 98/26830 | 6/1998 |
| WO | WO 98/33433 | 8/1998 |

OTHER PUBLICATIONS

Mark Kantrowitz, Erik Horskotte and Cliff Joslyn: "Answers to Frequently Asked Questions about Fuzzy Logic and Fuzzy Expert Systems" Version 1.24 last Modified Feb. 20, 1996, admitted prior art.

* cited by examiner

VENT VALVE ASSEMBLY

FIELD OF THE INVENTION

The present invention relates to a vent valve apparatus for use with a system for supplying breathable gas pressurised above atmospheric pressure to a human or animal.

The invention has been developed primarily for use in controlling the venting of washout gas in a continuous positive airway pressure (CPAP) gas delivery systems used, for example, in the treatment of obstructive sleep apnea (OSA) and similar sleep disordered breathing conditions. The invention may also be used in conjunction with suitable mask and gas delivery system for the application of assisted ventilation treatment.

The term "mask" is herein intended to include face masks, nose masks, mouth masks, appendages in the vicinity of any of these masks and the like.

BACKGROUND OF THE INVENTION

Treatment of OSA by CPAP flow generator systems involves the continuous delivery of air (or breathable gas) pressurised above atmospheric pressure to a patient's airways via a conduit and a mask. CPAP pressures of 4 cm $H_2O$ to 22 cm $H_2O$ are typically used for treatment of sleep disordered breathing due to OSA and/or central apnea, depending on patient requirements.

Treatment pressures for assisted ventilation can range up to 32 cm $H_2O$ and beyond, depending on patient requirements.

For either the treatment of OSA or the application of assisted ventilation, the pressure of the gas delivered to patients can be constant level, bi-level (in synchronism with patient inspiration and expiration) or autosetting in level. Throughout this specification the reference to CPAP is intended to incorporate a reference to any one of, or combinations of, these forms of pressure delivery.

The prior art method for providing CPAP treatment includes a vent for gas washout of the gas flow. The vent is normally located at or near the mask or in the gas delivery conduit. The flow of gas through the vent is essential for removal of exhaled gases from the breathing circuit. Adequate gas washout is achieved by selecting a vent size and configuration that will allow a minimum safe gas flow at the lowest operating CPAP pressure, which, typically can be as low as, around 4 cm $H_2O$ for adults and 2 cm $H_2O$ in paediatric applications.

Existing vent configurations include single or multiple holes, foam diffusers, slots and combinations thereof. A reference herein to a vent may be understood to include a reference to one or more holes, foam diffusers, slots or any combination of them.

The flow of gas from the gas delivery system through the vent to atmosphere creates noise as the delivered gas, and upon expiration the patient expired gas including $CO_2$, passes through the vent. Increasing CPAP pressure results in more gas passing through the vent which in turn creates more noise. Existing prior art vents produce excessive noise when CPAP pressures are raised above about 4 cm $H_2O$. This noise can adversely affect patient and bed-partner comfort. Existing vents are also inefficient as they allow more gas through the vent than is required for adequate exhaust gas washout and thereby require the flow generator to provide more flow than is necessary in order to maintain the required treatment pressure. Further, where treatment gas is being supplied, such as oxygen, surplus treatment gas is vented and thereby wasted unnecessarily. A similar waste occurs where the supplied gas is humidified.

It is an object of the present invention to overcome or at least ameliorate one or more of these deficiencies of the prior art.

SUMMARY OF THE INVENTION

Accordingly, the invention provides a vent valve apparatus for use with a system for supplying breathable gas pressurised above atmospheric pressure to a human or animal, the apparatus includes a gas washout vent, a vent valve adapted to progressively restrict the flow area of the washout vent, and a pressure sensitive vent valve control means adapted to progressively cause said vent valve to restrict the flow area of the gas washout vent in response to increases in the pressure of the gas supply, thereby substantially regulating the volumetric flow of gas and/or $CO_2$ gas through the washout vent over a range of gas supply pressures.

Preferably, the system supplies breathable gas to a human patient.

The breathable gas is desirably air.

In an embodiment of the invention, the gas washout vent consists of an orifice having the shape of an outwardly diverging truncated cone and the vent valve is a complementary cone shaped plug. The rim of the cone shaped orifice acts as a valve seat for the cone shaped plug.

Desirably, the pressure sensitive vent valve control means includes an elastic diaphragm connected to the vent valve such that displacement of the diaphragm results in displacement of the vent valve. In an embodiment, the diaphragm is produced from a rubber or other elastic diaphragm stretched over a circular orifice. The vent valve is preferably connected to the rubber by a connection means that allows for the stroke of the vent valve to be adjusted.

The vent valve is desirably attached to the centre of the rubber diaphragm by a connection means such as a rod, the rod being operatively connected to both the vent valve and the diaphragm.

In a preferred embodiment, the vent valve and diaphragm are directly connected by the rod. The rod is preferably rigid, such that movement of the diaphragm is directly proportional to the movement of the vent valve.

In another embodiment, the connection means include a lever assembly connecting the vent valve to the diaphragm so as to permit differing ratios of movement and mechanical advantage of the vent valve relative to the diaphragm.

Such an assembly can include a tension means that opposes the movement of the diaphragm caused by increasing gas supply pressure so as to bias the vent valve to a position where the flow area of the orifice is maximised.

It will be understood that the orifice covered by the diaphragm need not be circular and can be any convenient shape.

In one preferred configuration, the vent valve apparatus is provided in a branch connection from a mask. In another preferred configuration, the vent valve apparatus is provided in an air supply conduit substantially adjacent the mask.

In a further embodiment, the vent valve apparatus includes an aerodynamic member such as an aerofoil or wing. The member is disposed in the air supply conduit by a biased pivot mechanism and has an axis of rotation transverse to the direction of gas flow. Gas passing through the conduit causes the aerodynamic member to generate lift and to be rotatably displaced in proportion to the velocity of the gas flowing through the conduit. As the gas velocity increases the aerodynamic member produces increase lift and the resulting rotational displacement is transmitted to the vent valve which restricts the flow area of the washout vent. The vent valve is preferably biased open to a maximum washout vent flow area by a tension means such as a spring.

In a further preferred embodiment an aerodynamic member is suspended in a branch of the conduit and adapted for rotation about an axis transverse to the branch. Rotation around the axis is in response to the gas flow, which is proportional to the pressure in the conduit. The member is connected to the vent valve such that as the pressure in the conduit increases the rotational displacement of the aerodynamic member causes corresponding movement of the vent valve, resulting in a reduction of the flow area of the washout vent. A tension means is adapted to bias the vent valve, such as a spring, operates on the aerodynamic member to oppose the rotation caused by the gas flow on the aerodynamic member. The tension means biases the aerodynamic member in a rotational direction opposite to the direction induced by the gas flow entering the branch from the conduit.

BRIEF DESCRIPTIONS OF THE DRAWINGS

Preferred embodiments of the invention will now be described, by way of examples only, with reference to the accompanying drawings in which.

DESCRIPTION OF THE EMBODIMENTS

Figure 1:
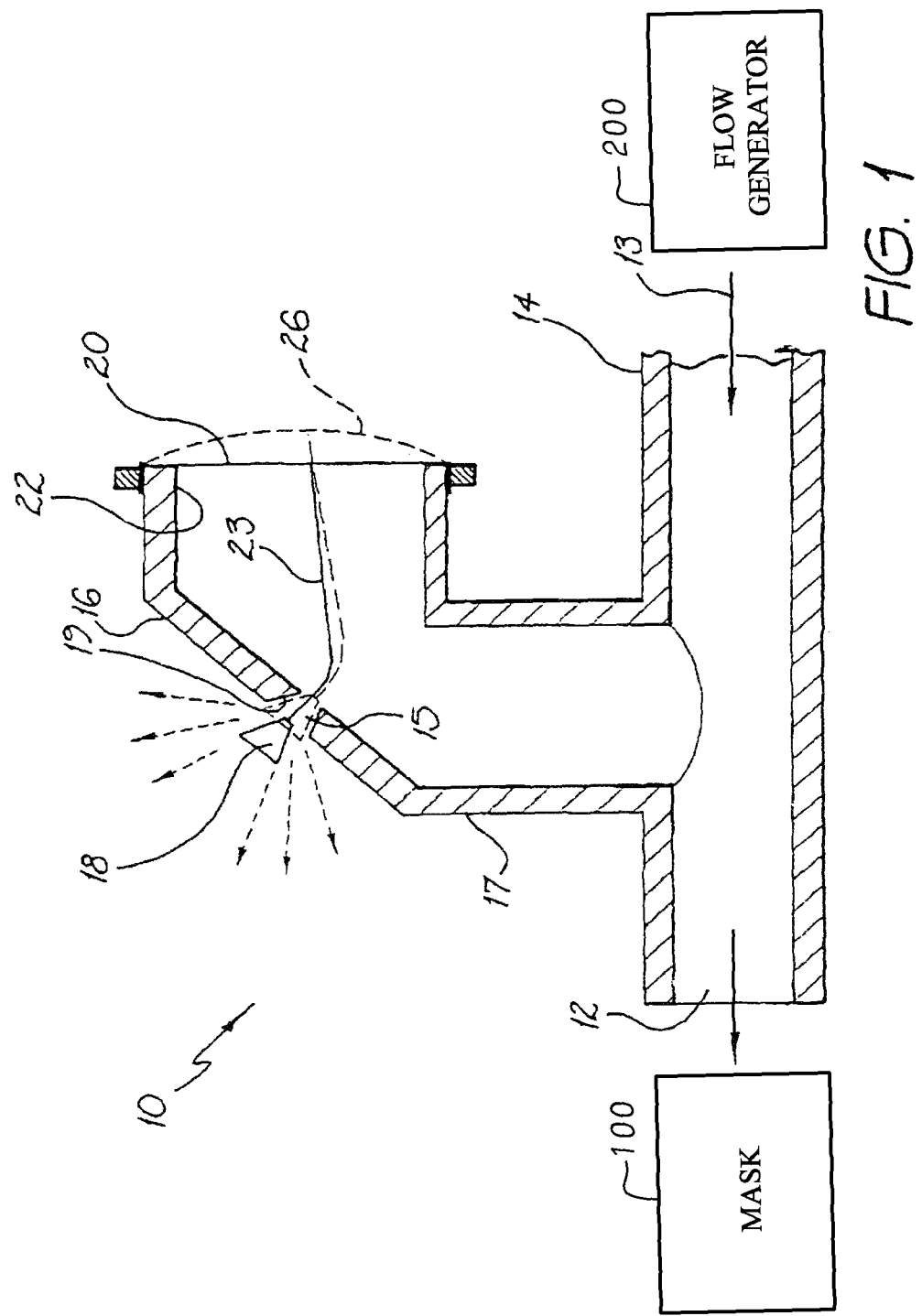
FIG. 1 is a schematic sectional side view of a vent valve apparatus according to the first embodiment of the invention.

Referring to FIG. 1, there is shown a vent valve apparatus 10 according to a first embodiment of the invention. The vent valve apparatus 10 is connected to a mask 100 at 12. The mask is adapted to receive a continuous supply of gas 13 above atmospheric pressure from a flow generator 200 through a flexible conduit 14. The apparatus 10 includes a gas washout vent, in the form of a substantially conical orifice 15 formed in a wall 16 of the pipe branch 17, and a vent valve in the form of a substantially conical plug 18. The rim 19 of the orifice 15 acts as a valve seat for the plug 18. The apparatus 10 also includes a pressure sensitive vent valve control means which includes an elastic diaphragm 20 stretched over a circular orifice 22 of the branch 17, and a rigid wire rod 23 connecting the plug 18 to the centre of the diaphragm 20.

In this embodiment, the plug 18 is conical and the orifice 15 is circular. In other embodiments (not shown), the plug and the orifice are other complimentary shapes.

The orifice 15 provides an outlet for the removal of gas upon patient expiration. Gas removal is aided by the continuous flow of gas pressurised above atmospheric pressure flowing through the conduit 14 and to atmosphere through the orifice 15.

As the air pressure in conduit 14 increases, corresponding increases occur in the air pressure adjacent diaphragm 20. These pressure increases cause diaphragm 20 to bulge to the position represented by phantom line 26. The displacement of the centre of the diaphragm 20 results in corresponding displacement in the plug 18, causing the plug 18 to be drawn into the orifice 15 thereby restricting the flow of gases through the vent orifice. In this way, the flow area of the vent is restricted at higher delivery pressures thereby reducing flow of gas through the orifice 15 compared to a fully open orifice.

The apparatus can be calibrated by adjusting the length of the wire rod 23 between the plug 18 and the diaphragm 20.

The vent valve apparatus 10 thereby maintains the airflow through the vent at, or at least near, the optimum safe minimum amount. This has the effect of reducing the noise produced at higher CPAP pressures, compared to the noise emitted by a similar orifice without the vent valve. A quieter vent improves patient and bed-partner comfort. An additional benefit provided by the invention is the reduction in the amount of wasted gas forced through the vent unnecessarily at higher CPAP treatment pressures.

A prototype of the first embodiment of the invention shown in FIG. 1 has been tested over a range of CPAP treatment pressures utilising the present Applicant's Sullivan™ flow generator made by ResMed Limited and Sullivan™ mask frame (fitted with Series 3 Sullivan™ Bubble Cushion™) modified in accordance with the teaching of this invention. This prototype was also tested without the conical plug 18. The results of the tests are summarised in the table below:

TABLE 1

Performance Comparison for Prototype Vent Valve Apparatus With and Without the Conical Plug

| | With | | Without | |
|---|---|---|---|---|
| CPAP Pressure cmH20 | Air Flow 1/m | Sound Pressure Level dB(A) | Air Flow 1/m | Sound Pressure Level dB(A) |
| 4 | 11.2 | 34.1 | 11.9 | 36.1 |
| 10 | 14.4 | 46.8 | 19.5 | 48.4 |
| 18.5 | 9.0 | 52.7 | 26.7 | 55.7 |

As the results show, the prototype vent valve according to the first embodiment of the invention maintained a substantially constant air flow through the vent over a wide range of CPAP treatment pressures compared to the large variation exhibited by a similar mask without the conical plug. Further, at all pressures, the noise produced by the mask using the vent valve apparatus according to the first embodiment of the invention was less than the same mask without the conical plug.

Figure 2:
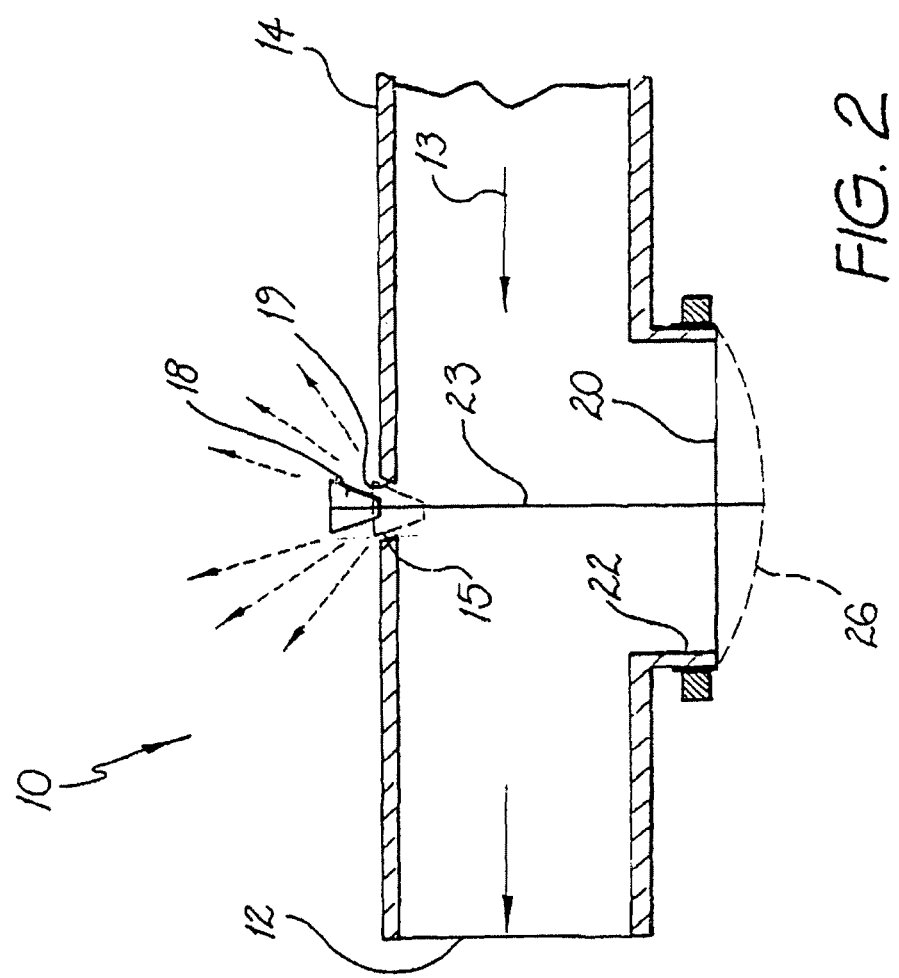
FIG. 2 is a schematic sectional side view of a vent valve apparatus is according to a second embodiment of the invention.

Referring now to FIG. 2, there is shown a vent valve apparatus according to a second embodiment of the invention. Like reference numerals to those used in FIG. 1 will be used to indicate like features in FIG. 2. This second embodiment functions in the same way as the first embodiment in that an increase in pressure in the conduit 14 causes the diaphragm 20 to bulge and draw the plug 18 into the washout valve orifice 15, thereby restricting the flow of gas through that orifice.

Figure 3:
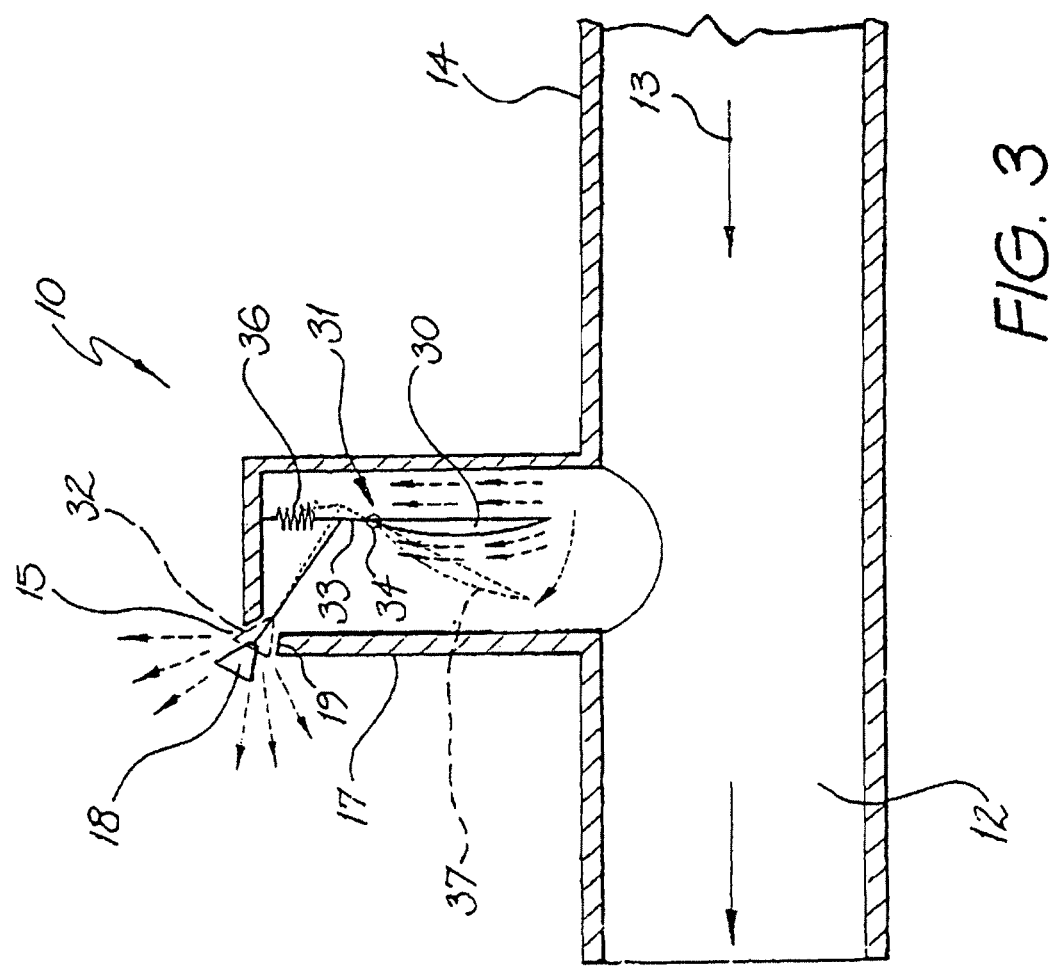
FIG. 3 is a schematic sectional side view of a vent valve according to a third embodiment of the invention.

A third embodiment of the present invention is shown in FIG. 3. Once again, like reference numerals are used to indicate like features. This third embodiment includes an aerodynamic member, in the form of wing 30, which is disposed in conduit branch 17 and adapted to pivot about an axis transverse to the direction of the gas flow along the conduit branch 17. The wing 30 is connected to a pivot mechanism, indicated generally at 31, which includes a connecting rod 33 and pilot joint 34. The connecting rod 33 and pivot joint 34 operatively connects the plug 18 to the wing 30, is used to bias the wing 30 and plug 18 to a position where the flow area of orifice 15 is maximized. As gas supply 13 is forced through the conduit 14, branch 17 and over the wing 30, the wing generates lift which opposes the spring and causes displacement of the wing to the position shown by phantom line 37, thereby drawing plug 18 into orifice 15 as shown by phantom line 32 and, thereby reducing the flow area of the gas washout orifice 15. Accordingly, the higher the pressure and flow rate of air passing through the branch 17 of the conduit 14, the more lift is produced by the wing and the more the flow area of the washout vent orifice 15 is restricted.

As with the earlier embodiments described above, this maintains a substantially constant air flow through the washout vent orifice.

Although the invention has been described with reference to specific examples, it will be appreciated by those skilled in the art that the invention may be embodied in many other forms.

I claim:

1. A CPAP apparatus for supplying pressurized breathable gas to a patient, comprising:
    a flow generator structured to generate a supply of pressurized gas;
    a mask adapted to provide a seal with the patient's face;
    a conduit that interconnects the flow generator and the mask; and
    a vent valve apparatus for gas washout, the vent valve apparatus structured to control gas washout based on the pressure of the gas supply,
wherein the vent valve apparatus includes a gas washout vent, a vent valve adapted to progressively move within the gas washout vent so as to progressively restrict the flow area of the gas washout vent, and a pressure sensitive vent valve controller adapted to progressively cause the vent valve to restrict the flow area of the gas washout vent in response to increases in the pressure of the gas supply, wherein the vent valve apparatus is structured to restrict gas washout in response to increases in the pressure of the gas supply.

2. The CPAP apparatus according to claim 1, wherein the vent valve apparatus is structured to expand gas washout in response to decreases in the pressure of the gas supply.

3. The CPAP apparatus according to claim 2, wherein the vent valve apparatus is structured to progressively expand gas washout.

4. The CPAP apparatus according to claim 1, wherein the gas washout vent and the vent valve include complementary shapes.

5. The CPAP apparatus according to claim 4, wherein the gas washout vent and the vent valve are cone-shaped.

6. The CPAP apparatus according to claim 1, wherein the vent valve apparatus is structured to progressively restrict gas washout.

7. The CPAP apparatus according to claim 1, wherein the flow generator is structured to generate pressurized gas in the range of about 4-22 cm $H_2O$.

8. The CPAP apparatus according to claim 1, wherein the flow generator supplies pressurized gas at a constant pressure.

9. The CPAP apparatus according to claim 1, wherein the flow generator supplies pressurized gas at two levels in synchronism with patient breathing.

10. The CPAP apparatus according to claim 1, wherein the flow generator continuously varies the level of pressurized gas.

11. The CPAP apparatus according to claim 1, wherein the vent valve apparatus is provided to the conduit.

12. The CPAP apparatus according to claim 1, wherein the vent valve apparatus is provided to the mask.

13. The CPAP apparatus according to claim 1, wherein the mask includes a face mask, nose mask, or mouth mask.

14. The CPAP apparatus according to claim 1, wherein the vent valve controller includes an elastic diaphragm connected to the vent valve such that displacement of the diaphragm results in displacement of the vent valve.

15. The CPAP apparatus according to claim 1, wherein the vent valve controller includes an aerodynamic member connected to the vent valve and rotatably displaceable such that rotatable displacement of the aerodynamic member results in displacement of the vent valve.

16. A CPAP apparatus for supplying pressurized breathable gas to a patient, comprising:
    a flow generator structured to generate a supply of pressurized gas;
    a mask adapted to provide a seal with the patient's face;
    a conduit that interconnects the flow generator and the mask; and
    a vent valve apparatus for gas washout, the vent valve apparatus structured to control gas washout based on the pressure of the gas supply,
wherein the vent valve apparatus includes a gas washout vent, a vent valve adapted to progressively move within the gas washout vent so as to progressively restrict the flow area of the gas washout vent, and a pressure sensitive vent valve controller adapted to progressively cause the vent valve to restrict the flow area of the gas washout vent in response to increases in the pressure of the gas supply, and wherein the vent valve apparatus is structured to expand gas washout in response to decreases in the pressure of the gas supply.

* * * * *